(12) United States Patent
Ohkubo et al.

(10) Patent No.: US 9,856,191 B2
(45) Date of Patent: Jan. 2, 2018

(54) PROCESS FOR PRODUCING FLUORINE-CONTAINING OLEFIN

(71) Applicant: DAIKIN INDUSTRIES, LTD., Osaka (JP)

(72) Inventors: Shun Ohkubo, Osaka (JP); Daisuke Karube, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 15/166,906

(22) Filed: May 27, 2016

(65) Prior Publication Data

US 2016/0355453 A1 Dec. 8, 2016

(30) Foreign Application Priority Data

Jun. 2, 2015 (JP) .................. 2015-112363

(51) Int. Cl.
- *C07C 17/25* (2006.01)
- *C07C 17/20* (2006.01)
- *B01J 23/46* (2006.01)
- *B01J 23/652* (2006.01)

(52) U.S. Cl.
CPC ............ *C07C 17/206* (2013.01); *B01J 23/46* (2013.01); *B01J 23/462* (2013.01); *B01J 23/464* (2013.01); *B01J 23/466* (2013.01); *B01J 23/468* (2013.01); *B01J 23/6522* (2013.01); *C07C 17/25* (2013.01)

(58) Field of Classification Search
CPC ............................. C07C 17/25; C07C 17/206
See application file for complete search history.

(56) References Cited

U.S. PATENT DOCUMENTS

| | | | | |
|---|---|---|---|---|
| 8,158,836 B2 * | 4/2012 | Pigamo | .................. | B01J 23/866 570/124 |
| 8,207,383 B2 * | 6/2012 | Deur-Bert | ............. | C07C 17/087 570/160 |
| 8,207,384 B2 * | 6/2012 | Wendlinger | ........... | B01J 23/866 570/160 |
| 8,398,882 B2 * | 3/2013 | Rao | .......................... | B01J 23/26 252/67 |
| 8,563,789 B2 * | 10/2013 | Elsheikh | ............... | C07C 17/206 570/123 |

| | | | |
|---|---|---|---|
| 2014/0364658 A1 | 12/2014 | Dubois | |
| 2015/0080619 A1 | 3/2015 | Deur-Bert et al. | |
| 2016/0052841 A1 | 2/2016 | Karube et al. | |

FOREIGN PATENT DOCUMENTS

| | | |
|---|---|---|
| JP | 2004-43410 | 2/2004 |
| JP | 2011-525925 | 9/2011 |
| JP | 2013-523734 | 6/2013 |
| JP | 2013-523882 | 6/2013 |
| JP | 2014-51512 | 3/2014 |
| JP | 2014-511350 | 5/2014 |
| JP | 2014-224089 | 12/2014 |
| JP | 2015-500327 | 1/2015 |
| JP | 2015-501800 | 1/2015 |
| JP | 2015-502390 | 1/2015 |
| WO | 2007/079431 | 7/2007 |
| WO | 2008/054781 | 5/2008 |
| WO | 2009/158321 | 12/2009 |
| WO | 2010/123154 | 10/2010 |
| WO | 2011/126679 | 10/2011 |
| WO | 2011/130108 | 10/2011 |
| WO | 2012/098421 | 7/2012 |
| WO | 2013/074324 | 5/2013 |
| WO | 2013/088195 | 6/2013 |
| WO | 2013/114015 | 8/2013 |

OTHER PUBLICATIONS

Extended European Search Report issued Oct. 13, 2016 in corresponding European Application No. 16171278.1.

* cited by examiner

*Primary Examiner* — Medhanit W Bahta
(74) *Attorney, Agent, or Firm* — Wenderoth, Lind & Ponack, L.L.P.

(57) ABSTRACT

In the production of fluorine-containing olefins using a chlorine-containing alkane or a chlorine-containing alkene as a starting material, a process for producing a plurality of useful fluorine-containing olefins with high selectivity using the same raw material, the same equipment, and the same conditions is provided. The present invention provides a process for producing fluorine-containing olefins, the process comprising reacting a chlorine-containing compound represented by a specific formula and anhydrous hydrogen fluoride in the presence of oxidative gas and a fluorination catalyst, wherein the fluorination catalyst is a catalyst in which at least one metal element M selected from the group consisting of Group VIII and Group IX is present together with chromium. This production process can simultaneously produce two or more fluorine-containing olefin compounds, including HFO-1234yf and HFO-1234ze, with high selectivity.

6 Claims, No Drawings

PROCESS FOR PRODUCING FLUORINE-CONTAINING OLEFIN

TECHNICAL FIELD

The present invention relates to a process for producing fluorine-containing olefins that can be used as refrigerants, etc.

BACKGROUND ART

Fluoroolefins represented by the formula: $CF_3(CX_2)_nCF=CH_2$, the formula: $CF_3(CX_2)_nCH=CHF$ (wherein n is an integer of 1 or more, and X is a halogen atom, such as fluorine or chlorine), or the like, are used for various applications, such as functional materials, solvents, refrigerants, and foaming agents. Further, these fluoroolefins are known to be compounds that have a useful structure as monomers or raw materials for producing functional polymers. For example, they are used as monomers for modifying ethylene-tetrafluoroethylene copolymers. Thus, these fluoroolefins are used for various applications and as various raw materials, and are highly useful compounds. Of these fluoroolefins, a compound represented by $CF_3CF=CH_2$ (HFO-1234yf) and a compound represented by $CF_3CH=CHF$ (HFO-1234ze) show increasing promise as refrigerant compounds with a low global-warming potential.

A fluoroolefin represented by an aforementioned formula is reportedly produced by, for example, reacting a chlorine-containing alkane or chlorine-containing alkene having the same number of carbon atoms, which is used as a starting material, with a fluorinating agent, such anhydrous hydrogen fluoride, in the presence of a catalyst (see PTL 1, mentioned below).

Moreover, of the fluoroolefins represented by the above formulas, HFO-1234yf is known to be produced by continuous vapor phase fluorination reaction of a chlorine-containing olefin, such as $CF_3CCl=CH_2$ (HCFO-1233xf), in the presence of a catalyst. HFO-1234yf produced in this manner has particularly attracted attention as a refrigerant with a low global-warming potential.

Furthermore, of the fluoroolefins represented by the above formulas, HFO-1234ze is known to be produced by continuous vapor phase fluorination reaction of a chlorine-containing olefin, such as $CF_3CH=CHCl$ (HCFO-1233zd), in the presence of a catalyst. For example, PTL 2 discloses that HFO-1234ze is produced by reacting HCFO-1233zd with hydrogen fluoride in the presence of a copper/chromium catalyst.

CITATION LIST

Patent Literature

PTL 1: WO2010/123154
PTL 2: JP2004-43410A

SUMMARY OF INVENTION

Technical Problem

As described above, it is known that HFO-1234yf or HFO-1234ze is produced by continuous vapor phase fluorination reaction of a chlorine-containing compound; however, the best raw materials used to produce the respective compounds are different, and the equipment and reaction conditions used are also different. Accordingly, when both compounds were simultaneously produced, the difference in their best production conditions caused lower selectivity of one of the compounds, and it was difficult to produce both compounds with high selectivity. Moreover, simultaneous production of both compounds required plant design suitable for each reaction, which problematically caused an increase in costs. Furthermore, when the purchase amount of raw materials used to produce the individual compounds is small, there is a concern that the purchase price of raw materials will increase.

Thus, in the production of fluorine-containing olefins using a chlorine-containing alkane or a chlorine-containing alkene as a starting material, if two or more fluoroolefins are simultaneously produced, the conversion of either compound is lower. Accordingly, it was difficult to obtain a plurality of compounds with high yield.

The present invention was made in consideration of the above situation, and an object thereof is to provide a process for producing fluorine-containing olefins using a chlorine-containing alkane or a chlorine-containing alkene as a starting material, the process capable of producing a plurality of useful fluorine-containing olefins with high selectivity using the same raw material, the same equipment, and the same conditions.

Solution to Problem

The present inventors conducted extensive research to achieve the above object, and consequently found that the above object can be achieved by performing a reaction using a catalyst in which at least one metal element M selected from the group consisting of Group VIII and Group IX is present together with chromium. Thus, the present invention has been completed.

More specifically, the present invention relates to the following process for producing fluorine-containing olefins.

1. A process for producing fluorine-containing olefins represented by Formula (7): $CF_3CA=CHB$, wherein one of A and B is F or Cl, and the other is H, the process comprising reacting a chlorine-containing compound and anhydrous hydrogen fluoride in the presence of oxidative gas and a fluorination catalyst, the chlorine-containing compound being at least one compound selected from the group consisting of:

a chlorine-containing alkane represented by Formula (1): $CX_3CClYCH_2Z$, wherein X is independently F or Cl, Y is H or F, when Y is H, Z is Cl or F, and when Y is F, Z is H;

a chlorine-containing alkane represented by Formula (2): $CX_3CH_2CHX_2$, wherein X is independently F or Cl, with the proviso that at least one of X is Cl;

a chlorine-containing alkene represented by Formula (3): $CX_3CCl=CH_2$, wherein X is independently F or Cl;

a chlorine-containing alkene represented by Formula (4): $CX_3CH=CHX$, wherein X is independently F or Cl, with the proviso that at least one of X is Cl;

a chlorine-containing alkene represented by Formula (5): $CH_2XCCl=CX_2$, wherein X is independently F or Cl; and a chlorine-containing alkene represented by Formula (6): $CHX_2CH=CX_2$, wherein X is independently F or Cl;

wherein the fluorination catalyst is a catalyst in which at least one metal element M selected from the group consisting of Group VIII and Group IX is present together with chromium.

2. The production process according to item 1, wherein the chlorine-containing compound is at least one member selected from the group consisting of HCC-240db, HCO- 1230xa, HCO-1230xf, HCFC-243db, HCFC-242dc, HCFO-1231xf, HCFO-1232xf, and HCFO-1233xf.

3. The production process according to item 1 or 2, wherein the fluorine-containing olefins include at least one member selected from the group consisting of HFO-1234yf and HFO-1234ze.

4. The production process according to any one of items 1 to 3, wherein the fluorine-containing olefins include HFO-1234yf and HFO-1234ze.

5. The production process according to any one of items 1 to 4, wherein the metal element M is an element of Period 5 or 6 of the periodic table.

6. The production process according to any one of items 1 to 5, wherein the metal element M is ruthenium.

7. The production process according to any one of items 1 to 6, wherein the molar ratio of the metal element M and chromium is 0.05:99.95 to 15:85.

Advantageous Effects of Invention

In the process for producing fluorine-containing olefins according to the present invention, a fluorination reaction of a chlorine-containing alkane or a chlorine-containing alkene is performed using a catalyst in which at least one metal element M selected from the group consisting of Group VIII and Group IX is present together with chromium. Thereby, two or more fluorine-containing olefin compounds, including, for example, HFO-1234yf and HFO-1234ze, can be simultaneously produced with high selectivity. Thus, according to the above production process, a plurality of useful fluorine-containing olefins can be produced with high selectivity using the same raw material, the same equipment, and the same conditions; it is not necessary to build many plants; and equipment costs and utility costs can be reduced. Furthermore, because such fluorine-containing olefins can be produced using the same raw material, the same equipment, and the same conditions, the purchase amount of raw materials used to produce the individual compounds is less likely to decrease, and the purchase price of raw materials is less likely to increase. It is thus advantageous in terms of cost. Therefore, the above production process is industrially advantageous as a process for producing fluorine-containing olefins.

DESCRIPTION OF EMBODIMENTS

An embodiment of the process for producing fluorine-containing olefins according to the present invention is described in detail below.

In the present embodiment, a chlorine-containing compound represented by a specific general formula is reacted with anhydrous hydrogen fluoride in the presence of oxidative gas and a fluorination catalyst to produce fluorine-containing olefins.

Specifically, fluorine-containing olefins represented by Formula (7): $CF_3CA\!=\!CHB$, wherein one of A and B is F or Cl, and the other is H, are produced by reacting a chlorine-containing compound and anhydrous hydrogen fluoride in the presence of oxidative gas and a fluorination catalyst, the chlorine-containing compound being at least one compound selected from the group consisting of:

a chlorine-containing alkane represented by Formula (1): $CX_3CClYCH_2Z$, wherein X is independently F or Cl, Y is H or F, when Y is H, Z is Cl or F, and when Y is F, Z is H;

a chlorine-containing alkane represented by Formula (2): $CX_3CH_2CHX_2$, wherein X is independently F or Cl, with the proviso that at least one of X is Cl;

a chlorine-containing alkene represented by Formula (3): $CX_3CCl\!=\!CH_2$, wherein X is independently F or Cl;

a chlorine-containing alkene represented by Formula (4): $CX_3CH\!=\!CHX$, wherein X is independently F or Cl, with the proviso that at least one of X is Cl;

a chlorine-containing alkene represented by Formula (5): $CH_2XCCl\!=\!CX_2$, wherein X is independently F or Cl; and a chlorine-containing alkene represented by Formula (6): $CHX_2CH\!=\!CX_2$, wherein X is independently F or Cl.

In particular, in the present embodiment, the fluorination catalyst is a catalyst in which at least one metal element M selected from the group consisting of Group VIII and Group IX is present together with chromium. Thereby, two or more fluorine-containing olefin compounds, including, for example, HFO-1234yf and HFO-1234ze, can be simultaneously produced with high selectivity.

The raw material compounds, reaction methods, and reaction products used in the production process of the present embodiment are described below.

Table 1 shows specific examples of the compounds represented by Formulas (1) to (7). Table 1 shows the symbol (abbreviation), structure, and chemical name of each compound. The compounds shown in Table 1 are just examples of the compounds represented by the above formulas. The compounds represented by Formulas (1) to (7) are not limited to the compounds shown in Table 1.

TABLE 1

| Formula | Symbol | Structure | Chemical name |
|---|---|---|---|
| (1) | HCFC-243db | $CF_3CHClCH_2Cl$ | 2,3-dichloro-1,1,1-trifluoropropane |
| (1) | HCFC-242dc | $CF_2ClCHClCH_2Cl$ | 1,2,3-trichloro-1,1-difluoropropane |
| (1) | HCFC-241dc | $CFCl_2CHClCH_2Cl$ | 1,1,2,3-tetrachloro-1-fluoropropane |
| (1) | HCC-240db | $CCl_3CHClCH_2Cl$ | 1,1,1,2,3-pentachloropropane |
| (2) | HCC-240fa | $CCl_3CH_2CHCl_2$ | 1,1,1,3,3-pentachloropropane |
| (2) | HCFC-243fa | $CF_3CH_2CHCl_2$ | 3,3-dichloro-1,1,1-trifluoropropane |
| (3) | HCFO-1233xf | $CF_3CCl\!=\!CH_2$ | 2-chloro-3,3,3-trifluoropropene |
| (3) | HCO-1230xf | $CCl_3CCl\!=\!CH_2$ | 2,3,3,3-tetrachloropropene |
| (3) | HCFO-1231xf | $CFCl_2CCl\!=\!CH_2$ | 2,3,3-trichloro-3-fluoropropene |
| (3) | HCFO-1232xf | $CF_2ClCCl\!=\!CH_2$ | 2,3-dichloro-3,3-difluoropropene |
| (4) | HCFO-1233zd | $CF_3CH\!=\!CHCl$ | 1-chloro-3,3,3-trifluoropropene |
| (4) | HCO-1230zd | $CCl_3CH\!=\!CHCl$ | 1,3,3,3-tetrachloropropene |
| (4) | HCFO-1231zd | $CFCl_2CH\!=\!CHCl$ | 1,3,3-trichloro-3-fluoropropene |
| (4) | HCFO-1232zd | $CF_2ClCH\!=\!CHCl$ | 1,3-dichloro-3,3-difluoropropene |
| (5) | HCO-1230xa | $CH_2ClCCl\!=\!CCl_2$ | 1,1,2,3-tetrachloropropene |
| (6) | HCO-1230za | $CHCl_2CH\!=\!CCl_2$ | 1,1,3,3-tetrachloropropene |

TABLE 1-continued

| Formula | Symbol | Structure | Chemical name |
|---|---|---|---|
| (7) | HCFO-1233xf | $CF_3CCl=CH_2$ | 2-chloro-3,3,3-trifluoropropene |
| (7) | HCFO-1233zd | $CF_3CH=CHCl$ | 1-chloro-3,3,3-trifluoropropene |
| (7) | HFO-1234yf | $CF_3CF=CH_2$ | 2,3,3,3-tetrafluoropropene |
| (7) | HFO-1234ze | $CF_3CH=CHF$ | 1,3,3,3-tetrafluoropropene |

(I) Raw Material Compound

In the present embodiment, at least one chlorine-containing compound selected from the group consisting of the compounds represented by Formulas (1) to (6) mentioned above is used as a starting material.

Specific examples of the chlorine-containing alkane represented by Formula (1): $CX_3CClYCH_2Z$ include 2,3-dichloro-1,1,1-trifluoropropane ($CF_3CHClCH_2Cl$ (HCFC-243db)), 1,2,3-trichloro-1,1-difluoropropane ($CF_2ClCHClCH_2Cl$ (HCFC-242dc)), 1,1,2,3-tetrachloro-1-fluoropropane ($CFCl_2CHClCH_2Cl$ (HCFC-241dc)), 1,1,1,2,3-pentachloropropane ($CCl_3CHClCH_2Cl$ (HCC-240db)), and the like.

Specific examples of the chlorine-containing alkane represented by Formula (2): $CX_3CH_2CHX_2$ include 1,1,1,3,3-pentachloropropane ($CCl_3CH_2CHCl_2$ (HCC-240fa)), 3,3-dichloro-1,1,1-trifluoropropane ($CF_3CH_2CHCl_2$ (HCFC-243fa)), and the like.

Specific examples of the chlorine-containing alkene represented by Formula (3): $CX_3CCl=CH_2$ include 2-chloro-3,3,3-trifluoropropene ($CF_3CCl=CH_2$ (HCFO-1233xf)), 2,3,3,3-tetrachloropropene ($CCl_3CCl=CH_2$ (HCO-1230xf)), 2,3,3-trichloro-3-fluoropropene ($CFCl_2CCl=CH_2$ (HCFO-1231xf)), 2,3-dichloro-3,3-difluoropropene ($CF_2ClCCl=CH_2$ (HCFO-1232xf)), and the like.

Specific examples of the chlorine-containing alkene represented by Formula (4): $CX_3CH=CHX$ include 1-chloro-3,3,3-trifluoropropene ($CF_3CH=CHCl$ (HCFO-1233zd)), 1,3,3,3-tetrachloropropene ($CCl_3CH=CHCl$ (HCO-1230zd)), and the like.

Specific examples of the chlorine-containing alkene represented by Formula (5): $CH_2XCCl=CX_2$ include 1,1,2,3-tetrachloropropene ($CH_2ClCCl=CCl_2$ (HCO-1230xa)), and the like.

Specific example of the chlorine-containing alkene represented by Formula (6): $CHX_2CH=CX_2$ include 1,1,3,3-tetrachloropropene ($CHCl_2CH=CCl_2$ (HCO-1230za)), and the like.

In the present invention, these raw material compounds can be used singly or in a combination of two or more.

(II) Reaction Method

In the production process of the present embodiment, a chlorine-containing compound mentioned above is used as a starting material, and the chlorine-containing compound is reacted with anhydrous hydrogen fluoride in the presence of oxidative gas and a fluorination catalyst.

In the production process of the present embodiment, the use of oxidative gas allows the reaction to proceed while the effect of suppressing the deterioration of the catalyst is sufficiently exhibited. Moreover, due to the use of a specific fluorination catalyst, described later, in an oxidative gas atmosphere, the conversion of the starting material can be maintained in a preferable range, and two or more fluorine-containing olefins can be easily produced with high selectivity by one reaction. Furthermore, due to the presence of oxidative gas in the reaction system, the amount of $CO_2$ produced as a by-product during the reaction can be reduced.

Examples of oxidative gas include oxygen (oxygen gas), chlorine (chlorine gas), and the like. The preferred oxidative gas is oxygen. In this case, the conversion of the starting material can be maintained in a preferable range, and two or more fluorine-containing olefins can be easily produced with higher selectivity.

The amount of oxidative gas supplied is preferably about 0.005 to 0.2 moles, and more preferably about 0.01 to 0.15 moles, per mole of the chlorine-containing compound used as a starting material.

The method for performing the reaction in the presence of an oxidative gas is not particularly limited. In general, an oxidative gas, such as oxygen, may be supplied to a reactor together with a chlorine-containing compound, which is a starting material. It is not limited thereto, and oxygen may be dissolved in a chlorine-containing compound and then supplied to a reactor.

The fluorination catalyst used in the present embodiment is a catalyst in which at least one metal element M selected from the group consisting of Group VIII and Group IX is present together with chromium.

The use of this catalyst allows the simultaneous production of two or more fluorine-containing olefin compounds with high selectivity.

The molar ratio of metal element M and chromium (the number of moles of metal M:the number of moles of chromium) is not particularly limited. For example, if the catalyst contains a metal element M and chromium within the range of 0.05:99.95 to 15:85, the selectivity of the individual fluorine-containing olefin compounds to be produced can be further improved.

The metal element M is preferably an element of Period 5 or 6 of the periodic table. In this case, the selectivity of the individual fluorine-containing olefin compounds to be produced can be further improved. In particular, when the metal element M is ruthenium, this effect is significantly exhibited.

The state of each metal element in the fluorination catalyst is not particularly limited, as long as it is a catalyst in which a metal element M is present together with chromium. For example, the fluorination catalyst may contain a metal element M and chromium in the form of oxides or fluorides. When the metal element M and chromium are oxides, these oxides may be fluorinated beforehand. In the production process of the present embodiment, the reaction is performed in the presence of hydrogen fluoride, and thus fluorination of the catalyst is thought to proceed during the reaction even when a fluorination treatment is not conducted beforehand.

When the metal element M present in the catalyst is ruthenium in an oxide form, examples thereof include crystalline ruthenium oxide, amorphous ruthenium oxide, and the like. The composition of ruthenium oxide is not particularly limited. For example, in the composition formula: $RuO_m$, m satisfies $1.5<m<4$, and preferably $2<m<2.75$.

When the chromium is in an oxide form, examples thereof include crystalline chromium oxide, amorphous chromium oxide, and the like. The composition of chromium oxide is not particularly limited. For example, in the composition formula: $CrO_n$, n satisfies $1.5<n<3$, and preferably $2<n<2.75$.

Fluorinated chromium oxide can be obtained by, for example, fluorination (HF treatment) of chromium oxide using hydrogen fluoride. The temperature of fluorination may be, for example, about 100 to 460° C. For example, chromium oxide can be fluorinated by supplying anhydrous hydrogen fluoride into a reactor filled with chromium oxide. The degree of fluorination of chromium oxide is not particularly limited. For example, fluorinated chromium oxide having a fluorine content of about 5 to 30 wt % can be preferably used.

The specific surface area of the fluorination catalyst is not limited, but is, for example, 20 $m^2$/g or more, and preferably 30 $m^2$/g or more. The fluorination catalyst can be in the form of a powder or pellet, and may be in another form as long as the form is suitable for the reaction. Among these, catalysts in pellet form are preferable.

Moreover, the fluorination catalyst may be not supported on a carrier, or may optionally be supported on a carrier. The carrier is not particularly limited, and is preferably, for example, at least one member selected from the group consisting of chromium fluoride, aluminum fluoride, fluorinated alumina, fluorinated activated carbon, and graphite carbon.

The fluorination catalyst may be used in a state where the raw material compound is in sufficient contact with the catalyst. For example, a method of forming a catalyst layer by immobilizing a catalyst in a reactor, a method of dispersing a catalyst in a fluidized bed, or other methods may be employed.

Anhydrous hydrogen fluoride may generally be supplied to a reactor together with a raw material compound. The amount of anhydrous hydrogen fluoride used is not particularly limited; however, in order to achieve a high selectivity of the target fluorine-containing olefins, it is preferably about 4 moles or more, and more preferably about 8 moles or more, per mole of the chlorine-containing compound used as a raw material.

The upper limit of the amount of anhydrous hydrogen fluoride is not particularly limited. An excessively large amount of hydrogen fluoride has little influence on selectivity and conversion. For example, the amount of anhydrous hydrogen fluoride is preferably about 100 moles or less per mole of the chlorine-containing compound used as a raw material. In this case, a decrease in productivity due to an increase in the amount of hydrogen fluoride to be separated during purification is less likely to occur. The amount of anhydrous hydrogen fluoride is more preferably about 50 moles or less per mole of the chlorine-containing compound used as a raw material.

In the above production process, the reaction temperature is not limited, and can be suitably adjusted depending on the type of raw material compound used; however, the reaction temperature can be generally within the range of 200 to 450° C. When the reaction temperature is within this range, the abovementioned catalyst deterioration-suppressing effect due to the use of oxidative gas can be further improved.

For example, when 2-chloro-3,3,3-trifluoropropene (HCFO-1233xf) is used as a raw material, the reaction temperature is preferably within the range of about 300 to 450° C., and more preferably about 325 to 400° C., in terms of making the conversion of the raw material and the selectivity of the target products within a preferable range. In this case, the amount of oxidative gas used is particularly preferably about 0.01 to 0.5 moles, and more preferably about 0.02 to 0.15 moles, per mole of 2-chloro-3,3,3-trifluoropropene (HCFO-1233xf).

The pressure during the reaction is not particularly limited, and the reaction may be performed under reduced pressure, ordinary pressure, or increased pressure. Although the reaction may be generally carried out at pressure near atmospheric pressure (0.1 MPa), it can also proceed smoothly under reduced pressure of less than 0.1 MPa. Furthermore, the reaction may be performed under increased pressure within a range in which the raw materials do not liquefy.

In a specific example of the reaction, the reaction is carried out by using a tubular flow reactor filled with a fluorination catalyst, and introducing a chlorine-containing compound used as a starting material, anhydrous hydrogen fluoride, and oxidative gas into the reactor. The equipment, including a reactor, used in the reaction may be those conventionally used for vapor phase fluorination.

The starting material supplied to the reactor may be in a gas phase when brought into contact with anhydrous hydrogen fluoride, or the starting material may be in a liquid phase when supplied. For example, when the starting material is liquid at ordinary temperature and ordinary pressure, the starting material is vaporized using a vaporizer (vaporization region), passed through a preheating region, and then supplied to a mixing region wherein the starting material is brought into contact with anhydrous hydrogen fluoride. The reaction is thereby conducted in a gas phase. The reaction may also be carried out by supplying the starting material in a liquid phase to a reactor, heating a catalyst layer filled in the reactor to a temperature higher than the gasification temperature of the starting material, and evaporating the starting material when the starting material enters a reaction region to react with hydrogen fluoride.

Each raw material used in the reaction may be directly supplied to the reactor, or may be supplied while allowing gas that is inert to the raw materials and catalyst, such as nitrogen, helium, or argon, to coexist. The concentration of inert gas may be about 0 to 80 mol % based on the total amount of the gas components introduced into the reactor, i.e., the total amount of the inert gas in addition to the chlorine-containing compound, anhydrous hydrogen fluoride, and oxidative gas.

Although the contact time is not limited, the contact time may be set while bearing in mind that the conversion of the reaction does not overly decrease, and that the production of by-products does not overly increase. For example, the contact time, which is represented by $W/F_0$, is preferably adjusted to about 0.5 to 70 g·sec/mL, and more preferably about 1 to 50 g·sec/mL. $W/F_0$ is the ratio of the amount of catalyst used W (g) to the total flow rate $F_0$ (flow rate at 0° C., 0.1 MPa: mL/sec) of the raw material gas supplied to the reaction system. The total flow rate of the raw material gas as used herein refers to the total flow of the chlorine-containing compound, anhydrous hydrogen fluoride, and oxidative gas, and, when used, inert gas, etc.

(III) Reaction Product

The above reaction produces fluorine-containing olefins represented by Formula (7): $CF_3CA=CHB$, wherein one of A and B is F or Cl, and the other is H. The structure of the produced fluorine-containing olefins is different from the structure of the chlorine-containing compound used as a starting material.

Specific examples of the fluorine-containing olefins represented by Formula (7) include 2,3,3,3-tetrafluoropropene (HFO-1234yf) represented by the formula: $CF_3CF=CH_2$, 1,3,3,3-tetrafluoropropene (HFO-1234ze) represented by the formula: $CF_3CH=CHF$, 2-chloro-3,3,3-trifluoropropene (HCFO-1233xf) represented by the formula: $CF_3CCl=CH_2$, and 1-chloro-3,3,3-trifluoropropene (HCFO-1233zd) represented by the formula: $CF_3CH=CHCl$.

For example, when $CF_3CHClCH_2Cl$ (HCFC-243db), $CF_2ClCHClCH_2Cl$ (HCFC-242dc), $CFCl_2CHClCH_2Cl$ (HCFC-241dc), $CF_3CCl=CH_2$ (HCFO-1233xf), $CF_2ClCCl=CH_2$ (HCFO-1232xf), $CFCl_2CCl=CH_2$ (HCFO-1231xf), $CH_2ClCCl=CCl_2$ (HCO-1230xa), $CCl_3CCl=CH_2$ (HCO-1230xf), or the like is used as a starting material, 2,3,3,3-tetrafluoropropene (HFO-1234yf) can be obtained as a main component.

Moreover, when $CCl_3CH_2CHCl_2$ (HCC-240fa), $CHCl_2CH=CCl_2$ (HCO-1230za), $CF_3CH=CHCl$ (HCFO-1233zd), $CCl_3CH=CHCl$ (HCO-1230zd), or the like is used as a starting material, 1,3,3,3-tetrafluoropropene (HFO-1234ze) can be obtained as a main component.

Because the reaction of the present embodiment uses, as a fluorination catalyst, a catalyst in which at least one metal element M selected from the group consisting of Group VIII and Group IX is present together with chromium, as described above, two or more fluorine-containing olefin compounds can be simultaneously produced with high selectivity. Even when the reaction is continued, catalytic activity hardly decreases, and high selectivity can therefore be maintained for a long period of time.

The fluorine-containing olefin compounds produced by the above reaction vary depending on the type of starting material, as described above, but preferably include at least one member selected from the group consisting of HFO-1234yf and HFO-1234ze. In this case, two or more fluorine-containing olefin compounds can be simultaneously produced with high selectivity. The fluorine-containing olefin compounds produced by the above reaction particularly preferably include HFO-1234yf and HFO-1234ze, because this combination can be produced with higher selectivity than other combinations.

The product can be collected, for example, from the outlet of the reactor. The collected product can be subjected to distillation or the like to thereby obtain the target fluorine-containing olefin compounds. The product may mainly contain 1,1,1,2,2-pentafluoropropane (HFC-245cb) as a by-product. Such a by-product can be easily converted into 2,3,3,3-tetrafluoropropene (HFO-1234yf) by dehydrofluorination reaction. Accordingly, in the production process of the present embodiment, even by-products can be effectively used.

According to the production process of the present embodiment, HFO-1234yf is produced as a fluorine-containing olefin, depending on the selection of the starting material. The products produced as by-products include, for example, at least one of HCFO-1224yd ($CF_3CFCHCl$) and HCFO-1224zb ($CF_3CHCFCl$). Therefore, the above production process can produce a composition containing HFO-1234yf and at least one of the compounds listed above.

Such a composition may be purified to collect HFO-1234yf with sufficient purity, or may be directly used, without purification, for various applications, such as refrigerants.

The HFO-1234yf content of the above composition is not particularly limited. For example, HFO-1234yf can be contained in an amount of 1 to 99.99 mass % based on the total amount of the composition.

The above composition may further contain HFO-1234ze ($CF_3CH=CHF$). HFO-1234ze is a fluorine-containing olefin component different from HFO-1234yf produced by the above reaction, and is produced with high selectivity.

In addition to HFO-1234ze, the above composition may contain at least one compound selected from the group consisting of CFC-13 ($CF_3Cl$), HFC-23 ($CHF_3$), HFC-32 ($CH_2F_2$), HCC-40 ($CH_3Cl$) HFC-152a ($CHF_2CH_3$), HFC-143a ($CF_3H_3$), $CF_3C\equiv CH$, vinyl chloride ($CH_2=CHCl$), HFC-245cb ($CF_3CF_2CH_3$), HFC-245fa ($CF_3CH_2CHF_2$), HFC-244bb ($CF_3CFClCH_3$), HCFC-244eb ($CF_3CHFCH_2Cl$), HCFC-244db ($CF_3CHClCH_2F$) HCFC-234bb ($CF_3CFClCH_2Cl$), HFC-236fa ($CF_3CH_2CF_3$), HCFO-1233zd ($CF_3CH=CHCl$), HCFO-1233xd ($CF_3CCl=CHCl$), HFO-1234yf dimer, HFO-1234yf trimer, carbon dioxide, and carbon monoxide. These compounds may be produced as by-products by the above reaction, or may be separately added to the product obtained by the reaction. Such a composition can also be preferably used for various applications or as raw materials.

When the above composition further contains HFO-1234ze, in addition to HFO-1234yf, the HFO-1234ze content is not particularly limited. For example, HFO-1234ze can be contained in an amount of 0.01 to 99 mass % based on the total amount of the composition.

EXAMPLES

The present invention is described in more detail below with reference to Examples; however, the present invention is not limited to the embodiments of these Examples.

Example 1

A fluorination catalyst containing chromium oxide and ruthenium oxide in combination and having a molar ratio of ruthenium (metal element M) and chromium of 5:95 was prepared. The fluorination catalyst (5.7 g) was placed in a metal reaction tube.

Next, the temperature of the reaction tube was increased to 350° C. Anhydrous hydrogen fluoride gas was supplied at a flow rate of 35 Nml/min, and oxygen gas was supplied as the oxidative gas to the reactor at a flow rate of 0.35 Nml/min. The reactor was maintained for 1 hour.

Thereafter, a fluorination reaction was performed by supplying gas of 2-chloro-3,3,3-trifluoropropene ($CF_3CCl=CH_2$ (HCFO-1233xf)) to the reaction tube at a flow rate of 3.5 Nml/min, thereby producing fluorine-containing olefins. About 15 hours later, the effluent gas from the reactor was first sampled, and analyzed by a gas chromatograph.

Example 2

A fluorination reaction was performed in the same manner as in Example 1, except that the flow rate of oxygen gas was changed to 0.07 Nml/min. Then, gas chromatographic analysis was conducted.

Example 3

A fluorination reaction was performed in the same manner as in Example 1, except that the fluorination catalyst was changed to a fluorination catalyst having a molar ratio of ruthenium (metal element M) and chromium of 1:99. Then, gas chromatographic analysis was conducted.

Example 4

A fluorination reaction was performed in the same manner as in Example 3, except that the flow rate of oxygen gas was changed to 0.07 Nml/min. Then, gas chromatographic analysis was conducted.

Comparative Example 1

A fluorination reaction was performed in the same manner as in Example 1, except that the fluorination catalyst was changed to chromium oxide ($Cr_2O_3$). Then, gas chromatographic analysis was conducted.

Table 2 shows the results of the gas chromatographic analysis conducted in each Example and Comparative Example. Table 2 also shows the ratio of the produced HFO-1234ze to the produced HFO-1234yf. The term "trace" in Table 2 indicates that the content is 1 ppm or more and 1% or less (concentration).

Therefore, it is demonstrated that the production process of the present invention can simultaneously produce two or more fluorine-containing olefin compounds, such as HFO-1234yf and HFO-1234ze, with high selectivity. Accordingly, a plurality of useful fluorine-containing olefins can be produced with high selectivity using the same raw material, the same equipment, and the same conditions; it is not necessary to build many plants; and equipment costs and utility costs can be reduced. Furthermore, because such fluorine-containing olefins can be produced using the same raw material, the same equipment, and the same conditions, the purchase amount of raw materials used to produce the individual compounds is less likely to decrease, and the purchase price of raw materials is less likely to increase. It is thus advantageous in terms of cost. Therefore, it can be said that the above production process is industrially advantageous as a process for producing fluorine-containing olefins.

TABLE 2

|  |  | Example 1 | Example 2 | Example 3 | Example 4 | Comparative Example 1 |
|---|---|---|---|---|---|---|
| Reaction temperature (° C.) | | 350 | 350 | 350 | 350 | 350 |
| Contact time (W/F0 g/Nml · sec) | | 9 | 9 | 9 | 9 | 9 |
| Hydrogen fluoride:raw material (molar ratio) | | 10:1 | 10:1 | 10:1 | 10:1 | 10:1 |
| Ruthenium content of catalyst (%) Ru/(Cr + Ru) | | 5 | 5 | 1 | 1 | 0 |
| Oxidative gas (catalyst deterioration suppressing agent) | | Oxygen | Oxygen | Oxygen | Oxygen | Oxygen |
| Oxidative gas relative to raw material (mol %) | | 10 | 2 | 10 | 2 | 10 |
| 1233xf conversion (GC %) | | 10 | 11 | 8 | 5 | 9 |
| HFO-1234ze/HFO-1234yf production molar ratio | | 0.5 | 0.8 | 0.8 | 0.7 | 0.06 |
| Selectivity (yield: %) | HFO-1234yf | 22 | 30 | 30 | 32 | 68 |
| | HFC-245cb | 5.7 | 8.6 | 8.8 | 7.5 | 21 |
| | HFO-1234ze | 11 | 23 | 23 | 21 | 3.9 |
| | HFC-245fa | trace | trace | trace | trace | trace |
| | HCFO-1233zd | 1.2 | 0.7 | 2.5 | 1.9 | 0.7 |
| | HFO-1243zf | trace | trace | trace | trace | 0.3 |
| | HCFO-1223xd | 1.7 | 1.1 | 2.1 | 1.2 | 0.2 |
| | HCFO-1224yd | trace | trace | trace | trace | trace |
| | HCFO-1224zb | trace | trace | trace | trace | trace |
| | HCFC-244bb | 4.4 | 8.7 | 2.3 | 5.3 | 0.9 |
| | HCFC-244db | trace | trace | trace | trace | trace |
| | HCFC-244eb | trace | trace | trace | trace | trace |
| | HCFC-234bb | trace | trace | trace | trace | trace |
| | HFC-236fa | 4.7 | 8.7 | 5.8 | 9.7 | trace |
| | $CF_3C{\equiv}CH$ | 0.2 | 0.3 | 0.2 | 0.5 | trace |
| | HFC-143a | 9.6 | 6.4 | 7.2 | 7.0 | trace |
| | HCFC-133a | 1.3 | 0.7 | 1.2 | 1.3 | trace |
| | $CH_3Cl$ | trace | trace | trace | trace | trace |
| | $CHF_3$ | trace | trace | trace | trace | trace |
| | $CF_3Cl$ | trace | trace | trace | trace | trace |
| | $C_2F_5CH{=}CH_2$ | trace | trace | trace | trace | trace |
| | HFO-1234yf dimer | trace | trace | trace | trace | trace |
| | HFO-1234yf trimer | trace | trace | trace | trace | trace |
| | $CO_2$ | 34 | 7.7 | 28 | 12 | 3.3 |
| | CO | trace | trace | trace | trace | trace |
| | Others | 4.5 | 3.4 | 4.6 | 1.4 | 1.2 |

The results of Table 2 reveal that each Example produced both HFO-1234yf and HFO-1234ze with high selectivity. On the other hand, in the Comparative Example, which used a fluorination catalyst that did not contain at least one metal element M selected from the group consisting of Group VIII and Group IX, the selectivity of HFO-1234yf was high, while the selectivity of other fluorine-containing olefins, including HFO-1234ze, was low.

The invention claimed is:

1. A process for producing two or more fluorine-containing olefins of Formula (7): $CF_3CA{=}CHB$, wherein one of A and B is F or Cl, and the other is H, the process comprising reacting a chlorine-containing compound and anhydrous hydrogen fluoride in the presence of oxidative gas and a fluorination catalyst to produce two or more fluorine-containing olefins, the chlorine-containing compound being at least one compound selected from the group consisting of:
a chlorine-containing alkane of Formula (1): $CX_3CClYCH_2Z$, wherein X is independently F or Cl, Y is H or F, when Y is H, Z is Cl or F, and when Y is F, Z is H;
a chlorine-containing alkane of Formula (2): $CX_3CH_2CHX_2$, wherein X is independently F or Cl, with the proviso that at least one of X is Cl;
a chlorine-containing alkene of Formula (3): $CX_3CCl=CH_2$, wherein X is independently F or Cl;
a chlorine-containing alkene of Formula (4): $CX_3CH=CHX$, wherein X is independently F or Cl, with the proviso that at least one of X is Cl;
a chlorine-containing alkene of Formula (5): $CH_2XCCl=CX_2$, wherein X is independently F or Cl; and
a chlorine-containing alkene of Formula (6): $CHX_2CH=CX_2$, wherein X is independently F or Cl;
wherein the fluorination catalyst is a catalyst in which at least one metal element M is present together with chromium,
wherein said at least one metal element M is an element selected from the group consisting of Group VIII and Group IX, and said at least one metal element M is an element of Period 5 or 6 of the periodic table.

2. The production process according to claim 1, wherein the chlorine-containing compound is at least one member selected from the group consisting of 1,1,1,2,3-pentachloropropane (HCC-240db), 1,1,2,3-tetrachloropropene (HCO-1230xa), 2,3,3,3-tetrachloropropene (HCO-1230xf), 2,3-dichloro-1,1,1-trifluoropropane (HCFC-243db), 1,2,3-trichloro-1,1-difluoropropane (HCFC-242dc), 2,3,3-trichloro-3-fluoropropene (HCFO-1231xf), 2,3-dichloro-3,3-difluoropropene (HCFO-1232xf), and 2-chloro-3,3,3-trifluoropropene (HCFO-1233xf).

3. The production process according to claim 1, wherein the fluorine-containing olefins include at least one member selected from the group consisting of 2,3,3,3-tetrafluoropropene (HFO-1234yf) and 1,3,3,3-tetrafluoropropene (HFO-1234ze).

4. The production process according to claim 1, wherein the fluorine-containing olefins include 2,3,3,3-tetrafluoropropene (HFO-1234yf) and 1,3,3,3-tetrafluoropropene (HFO-1234ze).

5. The production process according to claim 1, wherein the metal element M is ruthenium.

6. The production process according to claim 1, wherein the molar ratio of the metal element M and chromium is 0.05:99.95 to 15:85.

* * * * *